United States Patent [19]

Le Rouzic et al.

[11] Patent Number: 4,743,447
[45] Date of Patent: May 10, 1988

[54] COMPOSITION FOR DISINFECTING CONTACT LENSES

[75] Inventors: Daniel Le Rouzic, Ermont; Eric J. Laforte, Paris, both of France

[73] Assignee: L'Air Liquide Societe Anonyme pour l'Etude et l'Exploitation des Procedes Georges Claude, Paris, France

[21] Appl. No.: 41,611

[22] Filed: Apr. 23, 1987

Related U.S. Application Data

[63] Continuation of Ser. No. 820,380, Jan. 21, 1986, abandoned.

[30] Foreign Application Priority Data

Jan. 30, 1985 [FR] France ................................. 8501301

[51] Int. Cl.$^4$ .............................................. A61K 33/40
[52] U.S. Cl. ................................... 424/130; 514/839; 514/840
[58] Field of Search ................. 514/840, 839; 424/130

[56] References Cited

U.S. PATENT DOCUMENTS

| | | | |
|---|---|---|---|
| 3,908,680 | 9/1975 | Krezanoski | 252/102 |
| 3,912,451 | 10/1975 | Gaglia | 21/58 |
| 4,051,058 | 9/1977 | Böwing et al. | 424/130 |
| 4,051,059 | 9/1977 | Böwing et al. | 424/130 |

FOREIGN PATENT DOCUMENTS

| | | |
|---|---|---|
| 3134050 | 10/1983 | Fed. Rep. of Germany . |
| 7431512 | 9/1975 | France . |
| 1570492 | 2/1980 | United Kingdom . |

OTHER PUBLICATIONS

Chem. Abst. 86:145955a (1977)–Grosse et al.
Chem. Abst. 88:55113m (1978)–Grosse et al.
Chem. Abst. 96:223176v (1982)–Ren et al.

*Primary Examiner*—Douglas W. Robinson
*Attorney, Agent, or Firm*—Browdy and Neimark

[57] ABSTRACT

A disinfecting solution for contact lenses, both hard lenses and flexible lenses, comprising an aqueous solution of hydrogen peroxide and peracetic acid.

16 Claims, No Drawings

COMPOSITION FOR DISINFECTING CONTACT LENSES

This application is a continuation of application Ser. No. 820,380, filed 1-21-86, now abandoned.

FIELD OF THE INVENTION

The present invention relates to a composition for disinfecting contact lenses.

BACKGROUND OF THE INVENTION

The use of contact lenses involves a daily disinfecting treatment, and numerous and varied soaking and sterilization processes have been proposed.

Certain commercial compositions have as a base disinfecting agents, such as sodium mercurothiolate or chlorhexidine salts. According to U.S. Pat. No. 3,689,673, hydrophilic flexible contact lenses are treated by soaking in an aqueous containing from 0.001 to 0.1% chlorohexidine for a sufficient time and a sterilization is obtained in two to three hours with a solution of 0.001% concentration and in thirty minutes at a concentration of 0.01%.

At the present time, these disinfecting products are no longer used, because they have the drawback of facilitating the creation of deposits on the contact lenses.

Flexible, or soft, contact lenses are generally made from hydrophilic polymers. Now, the hydroxy groups of the lenses attract and retain substantial amounts of water in the plastic and this results in drawbacks during cleaning and sterilization. Moreover, additional difficulties are encountered in the treatment of hydrophilic flexible contact lenses because of their tendency to complex and concentrate certain preservatives used for conventional lenses, such as chlorobutanol, benzalkonium chloride, thimerosal, phenylmercuric nitrate... which are generally inactivated in the complex state. If the concentrated preservatives are released too quickly on the cornea, they can cause chemical burns. Consequently, the cleaning solutions presently available for conventional hard lenses are not suitable for flexible contact lenses.

The effectiveness of hydrogen peroxide as a disinfectant and its use as a germicidal agent in the disinfecting of numerous apparatuses and devices for medical use are well known.

Since 1972, hydrogen peroxide has been indicated as an advantageous agent in the sterilization of contact lenses as noted on page 247 of "Soft Contact Lens", published by C. V. Mosby Co., St. Louis. The majority of the products presently used have an aqueous solution base of hydrogen peroxide in a concentration on the order of 3%.

However, before a flexible contact lens is introduced into the eye, it must be rinsed several times in an isotonic buffered solution with a pH of 6.9 to 7.1. A correct rinsing, consisting of repeated immersions and rinsings, i.e. up to four, takes time—on the order of thirty or more minutes—, large volumes of saline solution and, depending on the user, gives no certainty of reproducibility. Further, the rinsing simply dilutes the hydrogen peroxide to a weaker concentration. Hydrogen peroxide, even in very small amounts on the order of about 10 ppm (parts per million) can cause eye irritation.

Consequently, processes for removal of hydrogen peroxide from flexible contact lenses have been studied.

French Patent No. 2.231.395 proposes a process for treatment of a flexible contact lens to perform its cleaning and sterilization and to treat it for its introduction into the eye after a complete sterilization, comprising placing the flexible contact lens in an aqueous sterilization solution having a hydrogen peroxide base containing an approximately isotonic concentration of sodium chloride and a catalytic amount of a decomposition catalyst for the hydrogen peroxide and in maintaining the contact lens in said solution until the concentration of hydrogen peroxide present is less than about 10 ppm. The flexible contact lens is thus effectively treated and sterilized by exposure to the action of the hydrogen peroxide for a period of ten minutes. However, the flexible contact lenses are then left in this aqueous solution of hydrogen peroxide for about six hours. By operating under these conditions the lenses are sterilized and the amount of detectable residual hydrogen is 20 ppm; to reduce the amount to less than 10 ppm, a single rinsing in the isotonic saline solution suffices.

European Patent No. 0 110 609 proposes a sterilizing treatment with hydrogen peroxide associated with the neutralization of the residual amounts of hydrogen peroxide with a solution of sodium pyruvate. The lenses are contacted with the hydrogen peroxide for at least about 5 minutes, preferably 10 minutes. They are then immersed in the sodium pyruvate solution, then washed with an isotonic aqueous sterile solution.

It has been found that hydrogen peroxide is not very effective in the sterilization of contact lenses, particularly as a fungicide. Additionally, certain deposits on the lenses are attributable to the presence of microorganisms.

French Patent No. 2.247.327 relates to the cleaning and restoration of plastic objects, particularly contact lenses. According to this process of complex practice, the lens is alternately made to undergo an expansion and a contraction to contribute to the removal of the residues and dirty marks. The ocular lens is put successively in contact with a first aqueous acid solution containing a peroxocompound, then with a second basic aqueous solution containing a peroxocompound, the the lens is put in contact with a non-ionic detergent and subjected to rinsing with water. The first and second solutions contain 0.1 to 15% by weight of a peroxocompound used for its great ability for cleaning and bleaching.

SUMMARY OF THE INVENTION

It is the object of the present invention to provide a disinfecting composition for contact lenses.

It is a further object of the present invention to provide a disinfecting composition suitable for use on soft, or flexible, contact lenses.

A disinfecting composition for contact lenses, either conventional hard lenses or soft, or flexible, lenses, has been found that has a much greater disinfecting ability than that of hydrogen peroxide, particularly as a fungicide. The composition is less irritating to the eye than the hydrogen peroxide solutions and the composition is compatible with the polymers used to make flexible lenses and makes it possible to prevent the creation of deposits on the lenses.

This stable, ready-to-use composition, having a hydrogen peroxide base, contains a low concentration of peracetic acid, $CH_3COOOH$. Very satisfactory results are obtained with a disinfection composition containing from 0.005 to 0.1% by weight of peracetic acid, 1 to 8% by weight of hydrogen peroxide and sufficient acetic acid for the system to reach equillibrium. Contents of 0.01 to 0.04% by weight, in particular of 0.01 to 0.015% by weight are particularly suited. A solution containing about 3% by weight of hydrogen peroxide, about 0.01% by weight of peracetic acid and a sufficient amount of acetic acid for equilibrium of the system can be cited.

The disinfecting composition further contains a non-ionic surfactant which is present in an amount of 0.001 to 0.005% by weight. The surfactants of the class of polyethanoxyalkylether, oxyethylene condensates and synthetic primary fatty alcohols, totally biodegradable, are perfectly suited to the application.

The composition contains de-ionized water in sufficient quantity to make 100%.

DETAILED DESCRIPTION OF THE INVENTION

The stable, ready-to-use disinfecting composition can be obtained by various methods, particularly by resorting to the preparation of peracetic acid from acetic acid and hydrogen peroxide, in proportions corresponding to the expected content of peracetic acid, then by adding the surfactant and de-ionized water, then aging until the system is balanced. It is also possible to prepare the immediately ready-to-use disinfecting composition from a stable commercial solution having a weak concentration of peracetic acid to which the other constituents of the composition are added, namely, hydrogen peroxide, acetic acid, the surfactant and diluting to the proper concentration with de-ionized water.

The disinfecting compositions according to the invention give excellent results in the daily cleaning and sterilization treatment of contact lenses, particularly flexible lenses.

According to this very simple and quick process, the lens is placed in the lens holder, put in contact with the disinfecting solution for a period on the order of a few minutes, preferably 2 to 5 minutes, 2 minutes being amply sufficient, then the lens is subjected to a short and simple rinsing with running water for a period on the order of 30 seconds, and the effectively disinfected contact lens is immediately ready to be applied on the eye.

Polarographic analysis sampled in a 0.1 molar lithium sulfate medium indicates that the concentration of residual peracetic acid in the lens after a soaking of ten minutes in a solution having 0.013% peracetic acid and rinsing 30 seconds is less than $4\pm1$ ppm and six hours later the same determination indicates $2\pm1$ ppm (parts per million) in a volume of 1.2 ml, knowing that the aqueous phase weighs 1.2 mg in the lens, which corresponds to a very low amount of residual peracetic acid.

The compositions according to the invention, in particular the final solution of example 1 having 0.013% peracetic acid, have been studied for their aseptic ability, irritating effect on the eye, compatibility with hydrophilic flexible lenses and deposits on the lenses.

Antiseptic Ability

The solution was tested according to the AFNOR T 72 151 standard on three bacterial strains:
*Pseudomonas aeruginosa:* CMCM-2-22
*Streptococcus faecalis:* ATCC-10541
*Klebsiella pneumoniae:* ATCC-10031
The results show that the solution reduces the population of these bacteria by a factor $10^5$ at 20° C., whereas 3% $H_2O_2$ has no bactericide activity according to the test protocol (reduction of $10^5$ after 5 minutes contact).

In regard to the fungicidal ability, the solution was tested according to the AFNOR NFT 72 200 standard on *Candida albicans* APCC-2091; for a reduction of the population of $10^7$ to $10^2$ germs/ml, less than five minutes of contact time with the solution of Example 1 is required, but more than 45 minutes of contact time with a solution of 3% $H_2O_2$.

The solution of example 1, diluted by half, i.e. containing 65 ppm of peracetic acid, makes it possible to obtain a reduction by a factor of $10^5$ in ten minutes of contact time, while a contact time greater than 120 minutes is required to obtain the same result with a 1.5% $H_2O_2$ aqueous solution.

On *Aspergillus niger* 218 IP, the same protocol applied to a population of $4\times10^6$ spores/ml requires 20 minutes of contact time to lower the population to $4\times10^1$ with the solution of example 1 and 50 minutes with a 3% $H_2O_2$ aqueous solution.

Irritating Effect on the Eye

The test for evaluation of the irritation to the eye was performed according to the method described by the order that appeared in the Official French Journal of Oct. 24, 1984. A lens treated with the antiseptic and non-rinsed product was applied for three minutes to the eye of a rabbit.

The effects caused after six hours, twenty-four hours and eventually daily for seven days were noted.

According to this test, the antiseptic products stand as follows:
3% $H_2O_2$ aqueous solution: slightly irritating.
Solution of example 1: very slightly irritating.

The solution of example 1 stands in the same class as a 0.9% sodium chloride aqueous solution.

It is surprising to find that the solution of example 1 has a very slightly pronounced irritating effect on the eye, despite the presence of peracetic acid and acetic acid, and it is unforeseeable that this effect is less than that of the 3% hydrogen peroxide and that said composition is non-necrosing.

Compatibility with Hydrophilic Flexible Lenses

The tests were performed on hydrophilic flexible lenses of polyhydroxymethacrylate; the lenses were soaked for sixteen days in the solution of example 1 and renewed daily with a test specimen kept in a 0.9% sodium chloride isotonic solution.

After about 400 hours of treatment, no significant change in the size of the lenses, their mechanical strength, their index of refraction and their elasticity was detected; no irreversible effect was observed, particularly on the hydration rate of the lenses, on which the index of refraction depends.

Deposits on the Lenses

On this point, the results are also fully satisfactory because no deposits were found on the lenses used and treated with the solution of example 1.

Non-limiting examples illustrating the invention are given below.

EXAMPLE 1

Into a one liter beaker 5 g of 99.7% purified acetic acid is measured, 41 g of a commercial solution of 70% hydrogen peroxide and 500 g of distilled, doubly ion-exchanged water are added; the solution thus obtained is stirred by a magnetic stirrer for about five minutes to homogenize the mixture. 200 mg of ethoxylated decyl alcohol are added to the solution and the 1,000 g solution bath is diluted with distilled, doubly ion-exchanged water and stirring is continued for five to ten minutes. The solution obtained is allowed to age, protected from dust, until the system is balanced.

The composition thus prepared has the following formula expressed in percent by weight:
Peracetic acid: 0.013%
Acetic acid: 0.487%
$H_2O_2$: 2.850%
Ethoxylated decyl alcohol (Commercial name "Empilan KA 5"): 0.002%
De-ionized water: 96.648%

After eight months of storage protected from dust and light at a temperature of 20±5° C., the strength of peracetic acid practically did not vary.

EXAMPLE 2

In a one liter beaker, 15 g of 99.7% purified acetic acid is measured, 42 g of a commercial solution of 70% hydrogen peroxide and 500 g of distilled doubly ion-exchanged water are added; the solution thus obtained is stirred by a magnetic stirrer for about five minutes to homogenize the mixture. 20 mg of ethoxylated decyl alcohol are added to the solution and the 1,000 g solution bath is diluted with distilled doubly ion-exchanged water. Stirring is continued for five to ten minutes and the solution is allowed to age as before.

At balance its composition by weight is as follows:
Peracetic acid: 0.034%
Acetic acid: 1.464%
$H_2O_2$: 2.920%
Ethoxylated decyl alcohol: 0.005%
De-ionized water: 95.568%

After eight months of storage, protected from dust and light at a temperature of 20±5° C., the strength of peracetic acid practically did not vary.

EXAMPLE 3

Into 500 g of distilled, doubly ion-exchanged water 5 g of a commercial solution having 2.5% peracetic acid, prepared according to European Patent No. 0 024 219, sold commercially under the trademark "Bactipal", 40 g of a commercial solution of 70% hydrogen peroxide and 4.6 g of acetic acid are introduced, the mixture is homogenized, then 20 mg of ethoxylated decyl alcohol are added, the 1,000 g solution is diluted with distilled, doubly ion-exchanged water and stirring is continued for five to ten minutes.

A solution is obtained of the following composition by weight:
Peracetic acid: 0.012%
Acetic acid: 0.448%
$H_2O_2$: 2.855%
Ethoxylated decyl alcohol: 0.002%
De-ionized water: 96.643%
immediately ready for use.

It will be apparent that changes may be made in the methods and compositions described above without departing from the scope of the invention, and that all matter contained in the above description is for purposes of illustration and not limitation.

What is claimed is:

1. A disinfecting composition for daily treatment of flexible contact lenses comprising a stable aqueous solution having equilibrium concentration of from about 0.01 to about 0.04 peracetic acid, from about 1 to about 3% by weight of hydrogen peroxide, and sufficient acetic acid for equilibrium.

2. The composition of claim 1, wherein the peracetic acid is present, at equilibrium in an amount ranging from about 0.01 to about 0.015% by weight.

3. The composition of claim 1, containing, at equilibrium, about 3% by weight of hydrogen peroxide, about 0.01% by weight of peracetic acid and sufficient acetic acid to maintain the equilibrium of the system.

4. The composition of claim 1, including, at equilibrium, from about 0.001 to 0.005% by weight of a non-ionic surfactant.

5. The composition of claim 4 wherein the non-ionic surfactant is a polyethanoxyalkylether.

6. A method of cleaning and sterilizing contact lenses, comprising contacting the lenses with an aqueous solution consisting essentially of, at equilibrium, from about 0.01 to about 0.04 peracetic acid, from about 1 to about 3% by weight of hydrogen peroxide, and sufficient acetic acid for equilibrium, for a period of from about two to five minutes, and rinsing the lenses with running water for up to about thirty seconds.

7. The composition of claim 1, consisting essentially of an aqueous solution consisting essentially of, at equilibrium, from about 0.01 to about 0.04 peracetic acid, from about 1 to about 3% by weight of hydrogen peroxide, and sufficient acetic acid for equilbrium.

8. The composition of claim 7, wherein the peracetic acid is present at equilibrium, in an amount ranging from about 0.01 to about 0.015% by weight.

9. The composition of claim 7, containing, at equilibrum, about 3% by weight of hydrogen peroxide, about 0.01% by weight of peracetic acid and sufficient acetic acid to maintain equilibrium.

10. The composition of claim 7, including, at equilibrium, from about 0.001 to 0.005% by weight of a non-ionic surfactant.

11. The method of claim 6, wherein the peracetic acid is present, at equilibrium, in an amount ranging from about 0.01 to about 0.015% by weight.

12. The method of claim 6, wherein the composition contains, at equilibrium, about 3% by weight of hydrogen peroxide, about 0.01% by weight of peracetic acid and sufficient acetic acid to maintain equilibrium.

13. The method of claim 6, wherein the composition includes, at equilibrium, from about 0.001 to 0.005% by weight of a non-ionic surfactant.

14. The method of claim 6, wherein the non-ionic surfactant is a polyethanoxyalkylether.

15. The composition of claim 7 consisting essentially of, at equilibrium, the following solution, by weight:
Peracetic acid: 0.012–0.034%
Acetic acid: 0.448–1.464%
$H_2O_2$: 2.850–2.920%
Ethoxylated decyl alcohol: 0.002–0.005%
De-ionized water: 96.568–96.648%.

16. In a stable, aqueous contact lens cleaning solution comprising a non-ionic surfactant, the improvement wherein said cleaning solution further comprises a microbiocidal agent consisting essentially of equilibrium concentrations of from about 0.01 to about 0.04% peracetic acid, about 1 to about 3% hydrogen peroxide, and sufficient acetic acid for equilibrium, by weight of said cleaning solution.

* * * * *